(12) United States Patent
Dumoulin et al.

(10) Patent No.: US 7,725,157 B2
(45) Date of Patent: May 25, 2010

(54) SYSTEM AND METHOD FOR INTERVENTIONAL PROCEDURES USING MRI

(75) Inventors: Charles Lucian Dumoulin, Ballston Lake, NY (US); Richard Philip Mallozzi, Ballston Lake, NY (US); Robert David Darrow, Scotia, NY (US); Harvey Ellis Cline, Schenectady, NY (US); Renee Ann Guhde, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 562 days.

(21) Appl. No.: 11/383,608

(22) Filed: May 16, 2006

(65) Prior Publication Data
US 2008/0009700 A1 Jan. 10, 2008

(51) Int. Cl.
*A61B 5/05* (2006.01)
(52) U.S. Cl. .................. 600/410; 600/407; 600/411; 600/420; 600/424
(58) Field of Classification Search .............. 600/407, 600/410–412, 422–424, 433, 508; 382/128
See application file for complete search history.

(56) References Cited
U.S. PATENT DOCUMENTS

| | | | | |
|---|---|---|---|---|
| 6,026,316 A * | 2/2000 | Kucharczyk et al. | ...... | 600/420 |
| 6,226,542 B1 * | 5/2001 | Reisfeld | ...... | 600/407 |
| 6,368,285 B1 * | 4/2002 | Osadchy et al. | ...... | 600/508 |
| 6,556,695 B1 * | 4/2003 | Packer et al. | ...... | 382/128 |
| 6,701,176 B1 | 3/2004 | Halperin et al. | | |
| 7,505,808 B2 * | 3/2009 | Anderson et al. | ...... | 600/411 |
| 2003/0199755 A1 * | 10/2003 | Halperin et al. | ...... | 600/411 |
| 2004/0097805 A1 * | 5/2004 | Verard et al. | ...... | 600/428 |
| 2004/0124838 A1 * | 7/2004 | Duerk et al. | ...... | 324/304 |

* cited by examiner

*Primary Examiner*—Long V Le
*Assistant Examiner*—Nigel Fontenot
(74) *Attorney, Agent, or Firm*—Joseph J. Christian

(57) ABSTRACT

An imaging and interventional system and methods are provided. The system comprises an imaging device for acquiring volumetric image data for an anatomical region of interest, a catheter for acquiring electrophysiological (EP) measurements of the anatomical region of interest, the catheter having at least one tracking coil for detecting signals indicative of a position of the catheter, and, a processor coupled to the catheter for receiving the EP measurements and signals indicative of the position of the catheter. The position of the catheter and EP measurements are combined and superimposed on a resultant image. The method comprises acquiring volumetric image data for an anatomical region of interest, acquiring position data for a catheter inserted in the region of interest, obtaining electrophysiological (EP) measurements for the region of interest and combining the image data, position data and EP measurements into a resultant image for use in the interventional procedure.

8 Claims, 4 Drawing Sheets

SYSTEM AND METHOD FOR INTERVENTIONAL PROCEDURES USING MRI

BACKGROUND

The invention relates generally to an imaging and interventional system, and in particular to a system for guiding and facilitating visualization during interventional, electrophysiology procedures using Magnetic Resonance Imaging (MRI).

Cardiac arrhythmias are a leading health problem, afflicting millions of people world-wide. The field of cardiac electrophysiology (EP) has grown rapidly in recent years to study and treat some of the most common forms of arrhythmia, such as atrial fibrillation (AF) and ventral tachycardia (VT). During EP procedures electrical catheters are inserted into the heart for electrical mapping, pacing and radio-frequency (RF) ablation.

Cardiac interventional procedures such as the ablation of tissue to treat atrial fibrillation and/or other cardiac conditions are complicated due to the lack of an efficient method to visualize the cardiac anatomy and its response to treatment in real-time. Simultaneous guidance of the catheters and visualization of the anatomy presents a significant challenge to the EP interventionalist, particularly when traditional X-ray methods are employed. One current practice is to visualize electrical data through point-by-point acquisition of electromagnetically (EM) tracked catheters. The tracked locations from the catheter are used to form an approximate rendition of the anatomy. Because information on catheter position is unregistered with true anatomical images, the resulting visualization depicts the anatomy poorly. Although possible, positional information from EM tracked catheters is not typically superimposed on any magnetic resonance (MR), computed tomography (CT), X-ray or ultrasound images. In some procedures, such as RF ablations, several hours are spent just to map the anatomy, without acquiring electrical data. Electrical data is thereafter obtained. Thus, current procedures, which require frequent manual tracking of the mapping catheter relative to the display, are tedious and often take several hours. Further, current procedures lack the ability to provide integrated images containing the electrical data important for EP procedures, as well as catheter position data and images of the anatomy.

There is a need to have real-time images of the anatomy superimposed with catheter positioning information and electrical activity measurements.

BRIEF DESCRIPTION

In a first aspect, an imaging and interventional system is provided. The system comprises a magnetic resonance imaging (MRI) device for acquiring volumetric image data for an anatomical region of interest, a catheter for acquiring electrophysiological (EP) measurements of the anatomical region of interest, the catheter having at least one tracking coil coupled to the MRI device for detecting signals indicative of a position of the catheter and the catheter having at least one electrode for detecting EP signals from the anatomical region of interest, and, a processor coupled to the catheter for receiving the EP measurements and signals indicative of the position of the catheter. The processor is configured to combine the signals indicative of the position of the catheter and the EP measurements in a resultant image including the anatomical region of interest.

In a second aspect, a method for imaging in an image-guided interventional procedure is provided. The method comprises acquiring volumetric image data for an anatomical region of interest, acquiring position data for a catheter inserted in the region of interest wherein the position data is obtained via at least one tracking coil disposed within the catheter, obtaining electrophysiological (EP) measurements for the region of interest and combining the image data, position data and EP measurements into a resultant image for use in the interventional procedure.

In a third aspect, a catheter for use in interventional image-guided procedures is provided. The catheter comprises a cable having a first end coupled to an imaging device and a second end for insertion into an anatomical region of interest, the insertion end being adapted for taking electrophysiological (EP) measurements, and at least one tracking coil disposed along the length of the catheter, wherein the tracking coil(s) are used to determine a position of the catheter within the region of interest and for determining respective locations where EP measurements are taken. The catheter is coupled to an imaging system for communicating signals indicative of the position of the catheter and the EP measurements for use in interventional image-guided procedures.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
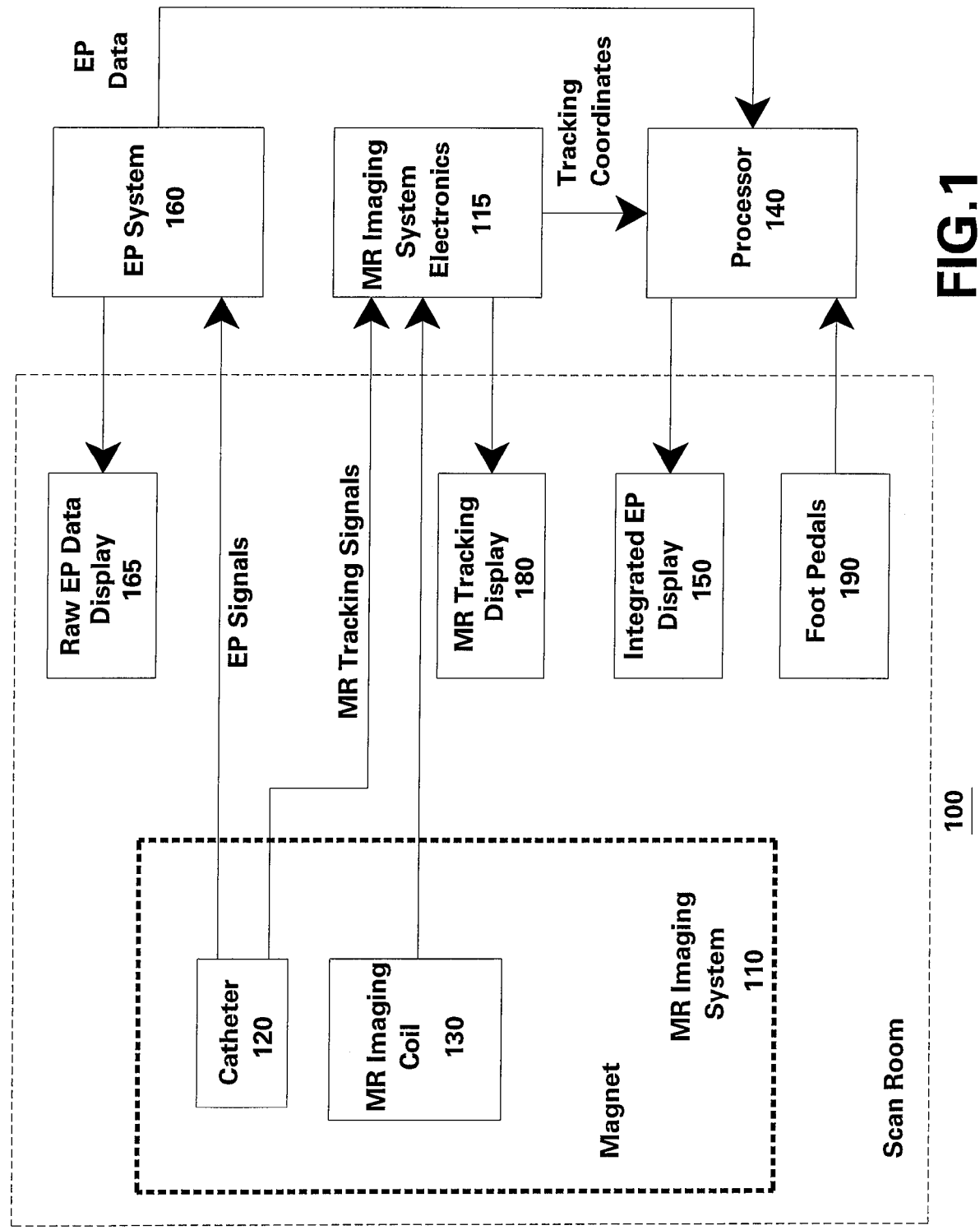
FIG. 1 is a block diagram of an imaging and interventional system in accordance with embodiments of the present invention.

Referring to FIG. 1, an interventional system 100 is provided. An imaging system 110, for example a magnetic resonance imaging (MRI) scanner, is used for acquiring volumetric image data for an anatomical region of interest. Anatomic data is collected using at least one MR Imaging coil 130. Anatomic signals detected by MR Imaging coil 130 are propagated to a set of imaging system electronics 115 where the signals are analyzed and one or more anatomic images are computed. A catheter 120 is used to acquire electrophysiological (EP) measurements of the anatomical region of interest. Catheter 120 includes tracking coils (125 of FIG. 2) to track the location of the catheter and corresponding location of EP measurement acquisition. Location signals detected by catheter 120 are propagated to imaging system electronics 115 where the signals are analyzed and the catheter's location is computed. The location of the catheter is displayed in real-time on MR Tracking Display 180. If desired, this location can be represented as an icon or graphic overlay on previously acquired MR image data. In addition, catheter comprises an electrode (not shown) for detecting EP signals. A more detailed description regarding the catheter will follow with reference to FIG. 2. The EP signals detected by catheter 120 are propagated to an EP system 160 for measuring, analyzing and delivering EP signals. EP system 160 propagates raw EP signals to a raw EP data display 165 for use by the operator. A processor 140 is coupled to the imaging system electronics 115 and to the EP system 160. The processor 140 is configured to combine the signals corresponding to the position of the catheter and EP measurements so that the combined signals are superimposed on a resulting image of the anatomical region of interest, such as a surface rendered three-dimensional (3D) image. Interventional system 100 further comprises a display 150, and foot pedals 190 for an operator of the system to control the EP system 160 and imaging system 110. Desirably, all components are co-located in an EP suite however certain components do not necessarily need to be co-located to employ embodiments of the present invention.

In an exemplary embodiment, imaging system 110 is an MRI scanner. Using MRI has several advantages, for example MRI provides excellent anatomical and physiological representations such as: visualization of soft tissue, for example the myocardium; three dimensional (3D) magnetic resonance angiography (MRA) of the great vessels; and, perfusion and diffusion weighted images. Further, tissue ablation (cryo, rf, laser, and the like) is easily visualized, catheters can be followed in real-time, and 3D localization is registered with MR images. Additionally, MRI does not require X-rays and therefore enables significant reduction of ionizing radiation needed in the long procedures using current methods. Further, MRI in the heart has proven very effective when measuring important physiological information, such as ejection fraction and cardiac wall motility. MRI has also been shown to provide excellent visualization of infarcted heart muscle using a variety of techniques including measuring the delay in signal enhancement that occurs after the injection of a T1-shortening MR contrast agent.

While embodiments of the present invention will be described using MRI, it is to be appreciated that the methods and systems described herein may be modified for other imaging systems as advances in X-ray dose reduction are developed. Thus, in further embodiments, imaging system 110 may be a computed tomography (CT), an X-ray or an ultrasound imaging system. In additional further embodiments, hybrid systems for interventional procedures may comprise combinations of MRI, CT, X-ray and ultrasound imaging systems.

During an MR imaging session, the patient is placed inside a strong magnetic field generated by a large magnet. Magnetized protons within the patient, such as the nuclei of hydrogen atoms, align with the magnetic field produced by the magnet. A particular slice of the patient is exposed to radio waves that create an oscillating magnetic field perpendicular to the main magnetic field at the magnetic resonance frequency (commonly called the Larmor frequency) of the magnetized protons. The slices can be taken in any plane chosen by the physician or technician (hereinafter the "operator") performing the imaging session. The protons within the selected slice in the patient's body first absorb the radio waves by moving out of alignment with the field. As the protons return to their original state (before excitation), diagnostic images based upon the waves emitted by the patient's body are created in a fashion well known to those skilled in the art. Like CT image slices, MR image slices can be reconstructed to provide an overall picture of the body area of interest. Traditionally, parts of the body that produce a high signal are displayed as white in an MR image, while those with the lowest signals are displayed as black. Other body parts that have varying signal intensities between high and low are displayed as some shade of gray.

Processor 140 is configured to perform computations in accordance with embodiments of the present invention which will be described in greater detail below. Processor 140 is also configured to perform computation and control functions for well-known image processing techniques such as reconstruction, image data memory storage, segmentation and the like. Processor 140 may comprise a central processing unit (CPU) such as a single integrated circuit, such as a microprocessor, or may comprise any suitable number of integrated circuit devices and/or circuit boards working in cooperation to accomplish the functions of a central processing unit. Processor 140 desirably includes memory. Memory within processor 140 may comprise any type of memory known to those skilled in the art. This includes Dynamic Random Access Memory (DRAM), Static RAM (SRAM), flash memory, cache memory, etc. While not explicitly shown in FIG. 1, the memory may be a single type of memory component or may be composed of many different types of memory components. Processor 140 is also capable of executing the programs contained in memory and acting in response to those programs or other activities that may occur in the course of image acquisition and image viewing. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to perform a sequel to provide an output in response to given input signals.

In an embodiment of the catheter for use in interventional image-guided procedures, the catheter comprises a cable have a first end coupled to an imaging device and a second end for insertion into an anatomical region of interest, the insertion end being adapted for taking electrophysiological (EP) measurements, and at least one tracking coil disposed along the length of the catheter, wherein the tracking coil(s) are used to determine a position of the catheter within the region of interest and for determining respective locations where EP measurements are taken. The catheter is coupled to an imaging system for communicating signals indicative of the position of the catheter and the EP measurements for use in interventional image-guided procedures.

Figure 2:
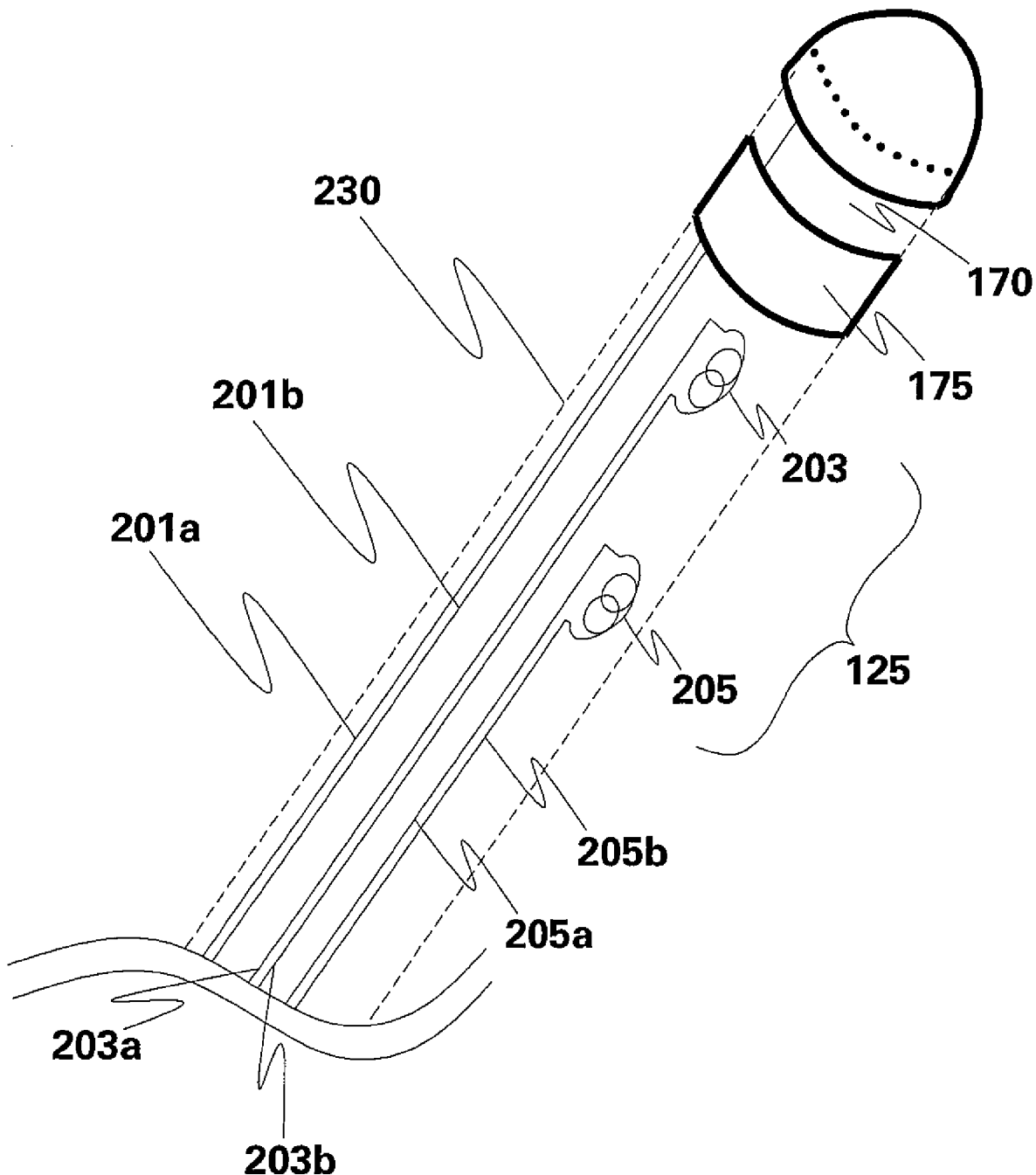
FIG. 2 is an illustration of a catheter for use in imaging and interventional procedures in accordance with embodiments of the present invention.

Referring further to FIG. 2, a schematic representation of catheter 120 is shown. Catheter 120 is comprised of a tip electrode 170, a ring electrode 175 and tracking coils 125 which, in this embodiment, comprise two tracking solenoids 203 and 205. EP signals detected by tip electrode 170 and ring electrode 175 are propagated to the EP system via conductors 201*a* and 201*b*. Solenoids 203 and 205 are constructed to propagate detected MR signals indicative of the position of the catheter to system electronics (115 of FIG. 1) via conductors 203*a*, 203*b*, 205*a* and 205*b*. The tip electrode 170, ring electrode 175, solenoids 203 and 205 as well as their associated conductors are housed in catheter shell 230. In the embodiment shown in FIG. 2, one tip electrode, one ring electrode and two tracking coils are shown for illustrative purposes. The number of electrodes and tracking coils in the present invention is not constrained to that shown in the figure. Rather, the scope of the present invention is intended to cover all embodiments having one or more electrodes and one or more tracking coils.

Figure 3:
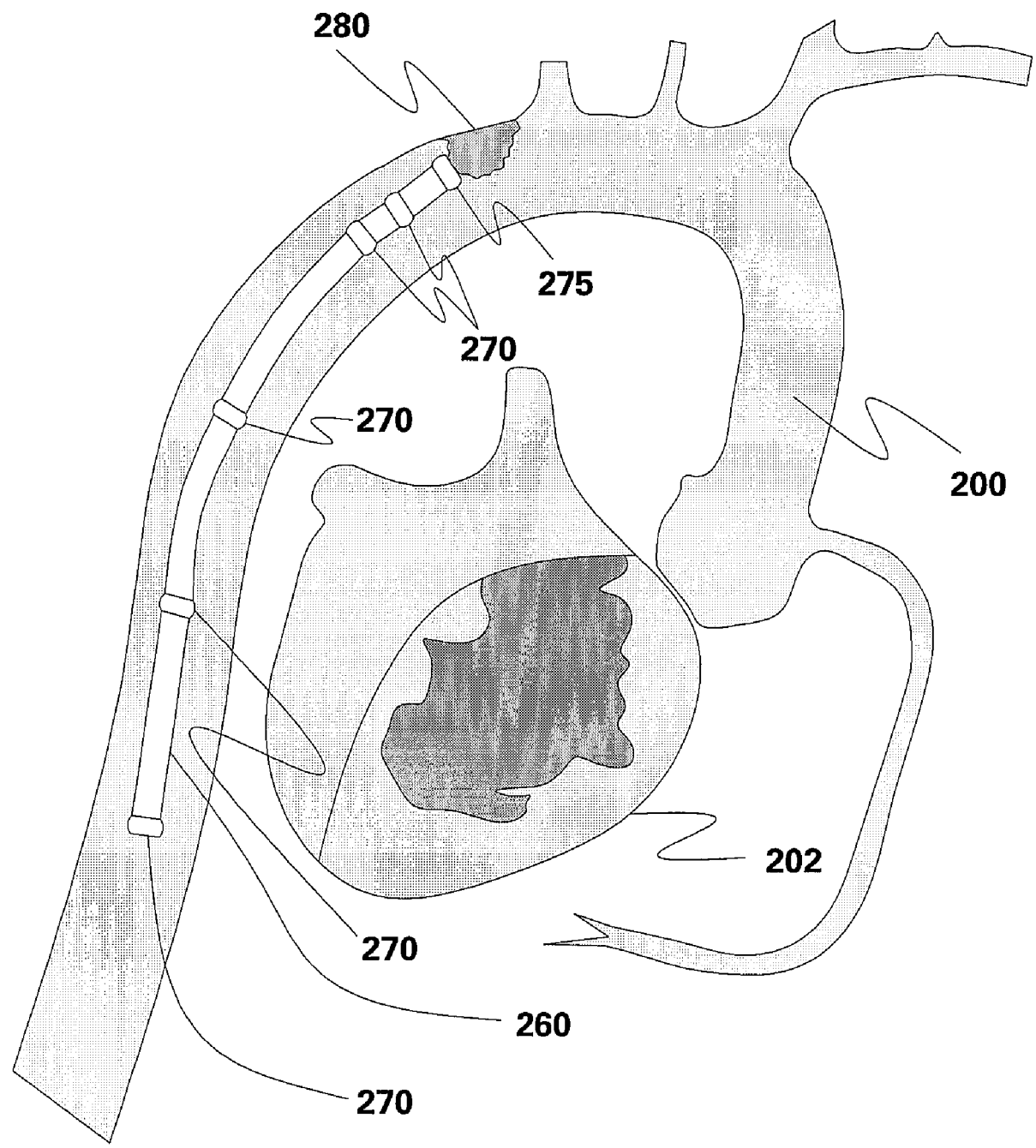
FIG. 3 is an illustration of a vascular phantom showing placement of a catheter in accordance with embodiments of the present invention; and, FIG. 4 is an illustration of a surface-rendered and color-mapped display to which embodiments of the present invention are applicable.

Referring further to FIG. 3, an illustration of an embodiment of catheter and tracking coils is shown in a segment of region of interest 200 (e.g. an aorta arch phantom) and 202 (e.g. heart phantom). In FIG. 3, the MR image data has been processed and rendered for viewing as a surface. Within this surface rendition 260 of catheter 120 from FIG. 1 is shown. Each coil in catheter 260 is illustrated as a ring 270 in the display. The location of the catheter tip (which is also the location of the tip electrode 170 of FIG. 2) is interpolated from the location of the two end-most coils and is shown as an end-ring 275. In an embodiment for display, the color of the rendered surface 200 is white except in those regions in which EP data has been collected. Color mapping will be discussed in greater detail with reference to FIG. 4. When EP data is collected, processor 140 of FIG. 1 uses the location information of the tracking coils to compute the location of tip electrode and colors a selected region 280 of the surface rendering with a color that reflects a desired EP parameter such as voltage or delay time. In one embodiment of the present invention the selected region of the surface is computed by determining the intersection of the surface with a sphere of a selected radius at the location of tip electrode.

Figure 4:
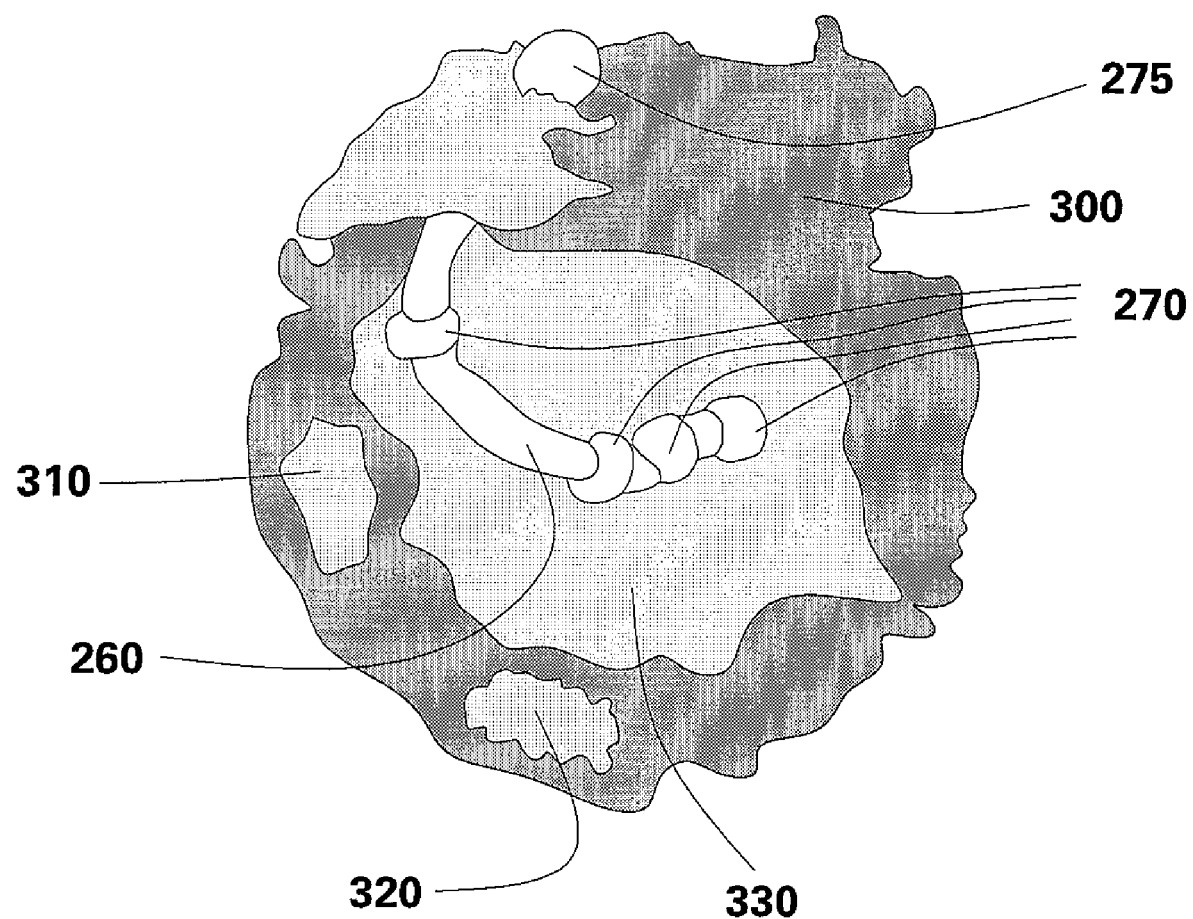

FIG. 4. is an illustration of a surface rendering 300 of the left atrium of a pig heart which has been catheterized according to the present invention. As shown, EP information is displayed as different colored regions 310, 320 and 330 on a surface rendition 300 of anatomy obtained from MR images.

Referring further to FIGS. 1 and 2, in one embodiment of the present invention, catheter 120 is made of MRI compatible material (i.e. material that will not interfere with the magnetic field) and includes a plurality of tracking coils 125. Catheter 120 has an outer circumference that is compatible for interventional cardiac procedures, desirably in the range of about 2 French to about 8 French. If desired, the inner diameter of catheter 120 is adapted to house deflection wires and other wires such as cables coupled between the tracking coils 125 and imaging system 110. Further, catheter 120 is adapted to be sufficiently flexible for guidance through vascular structures, such as the heart. Further, catheter 120 is adapted to take EP measurements as described herein. Each of the tracking coils 125 is configured to collect MR signals for use by processor 140 in tracking the location of the catheter in a well-known manner. In one embodiment, there are three (3) tracking coils 125 each being connected to independent receivers in imaging system 110 by miniature cables within catheter 120. In another embodiment, there are five (5) tracking coils. The number of coils is selectable in order to optimize point-source tracking procedures to provide three-dimensional coordinates of the catheter device. The number of coils that can be simultaneously tracked is limited only by the number of receivers in the MR system. Further, more than one interventional device may be tracked using the methods described herein. More than one interventional device and respective tracking coils may be tracked and located by coupling the tracking coils to independent receivers in imaging system. In a further embodiment, two (2) catheters are employed where a first catheter is used for an interventional cardiac procedure such as ablation as described above and a second catheter is used to stimulate the heart, in a pace-maker manner, during the interventional procedure.

Referring further to FIG. 2, catheter 120 comprises a tip electrode 170 at the tip of the catheter 120, where the tip electrode 170 is situated at the insertion end of catheter 120. Tip electrode 170 is configured for taking EP measurements with the catheter. Locating a tracking coil near tip electrode 170 provides information regarding the location where EP measurements are obtained such that the tracking coil will provide a corresponding EP measurement location. The ring electrode 175 is positioned at a selected distance from the tip electrode 170 to provide an electrical reference for the EP measurement.

Tracking of an interventional device in MRI is performed either by passive tracking or active tracking. In both techniques, processor 140 employs known MR tracking algorithms for locating a device within an MR image. In passive tracking, steps are taken to make the device appear with altered signal intensity in a rapidly acquired MR image. For example, the material of the device may be chosen to have a magnetic susceptibility that differs somewhat from the tissue being imaged so that the signal void from the device becomes distinguishable in the resulting image. In active tracking, a signal is selectively detected or emitted from the interventional device. Several approaches are possible. In embodiments of the present invention, tracking coils 125 enables MR signals to be detected at the various locations of tracking coils 125 along catheter 120 thereby enabling location of catheter 120 within a region of interest, such as a heart or part of the heart. Locating a device using active MR tracking relies on the same fundamental principle as that used in MR imaging. In the presence of a magnetic field gradient, the Larmor frequency of each spin within the patient or subject varies along the axis of gradient. The MR signal in an MR tracking procedure is detected by a small coil (tracking coil 125) embedded in the device, which is capable of receiving signals from a limited volume. Once the MR tracking data is acquired, it can be used in a number of ways. For example, MR tracking icons can be generated and superimposed upon a reference image or resultant image.

Tracking coils 125 are constructed to have the sensitivity to act as a receive coil that is compatible with imaging system 110 (FIG. 1). Due to the relatively small size of the inner diameter of catheter 120, tracking coil 125 may comprise simple coils constructed without tuning and matching elements yet still have sufficient sensitivity for MR tracking. In one embodiment, tracking coil 125 comprises a solenoid attached to a coaxial cable. In this embodiment, no tuning or matching capacitors are employed. In another embodiment, multiple tracking coils 125 are provided in order to propagate several different detected MRI signals to the imaging system 110. In this embodiment, the signals detected from the multiple tracking coils 125 are coupled to corresponding multiple receivers within the imaging system. However, it is possible to use a single receiver but measures will need to be taken to address potential overlapping signals. In one embodiment, sensitivity of each coil can be made to have a different sensitivity such as by constructing each coil with a different number of turns.

In order to effect the MR signal detection from the tracking coils 125 as described above, the imaging system 110 will employ any of a variety of known MRI pulse sequences for determining the location of a MR signal source from, for example, each of the tracking coils 125. In one embodiment, a pulse sequence comprises a simple non-selective rf pulse and a readout magnetic field gradient pulse that is repeated a selected number of times, e.g. 3, to obtain the location of the signal source in the X, Y and Z directions. A gradient-recalled echo is then generated with a frequency-encoded gradient pulse applied on a single axis. Frequency analysis of the MR signal detected in the presence of this magnetic pulse is performed to determine the location of the coil along the axis of the applied gradient. The three-dimensional coordinates of the device (catheter) can be determined by repeating the process using orthogonal magnetic field gradient pulses. It is to be appreciated that one skilled in the art may apply a number of known pulse sequences to obtain the 3D coordinates of the device. This embodiment is provided as an example. Other embodiments may employ gradient recalled echo (GRE), spin echo (SE), fast spin echo (FSE), steady state free precession (SSFP), and/or echo-shifted fast GRE (ESF-GRE) pulse sequences. Furthermore, the tracking information may be superimposed upon any number of MR images including: gradient recalled echo (GRE), spin echo (SE), fast spin echo (FSE), steady state free precession (SSFP), echo-shifted fast GRE (ESFGRE) and two-dimensional phase contrast (PC) magnetic resonance angiography (MRA) images either individually or in combination.

Using the methods described above to obtain the 3D coordinates requires fewer gradient pulses than is necessary for conventional MR imaging. Furthermore, the gradient pulses for detecting signals indicative of the position of the catheter may be desirably selected to be substantially weaker than gradient pulses needed to generate images. Gradient pulses are inversely proportional to the field of view (FOV). Thus, by employing fewer and weaker gradient pulses, acoustic noise is reduced to the patient or subject undergoing imaging and interventional procedures thereby desirably reducing the need for hearing protection by the subject or user of the system. Further, since the gradient pulses are substantially less than is needed for obtaining image data, there is advantageously no need for additional filters or thermal measures to compensate for the gradient pulses.

An additional desirable aspect of the present invention with respect to high-speed imaging methods for device localization is that with "point source" tracking greater tracking frame rates are obtained with fewer rf pulses, each having potentially less rf power. With a "point source" approach, each three-dimensional localization can be obtained with as few as three low flip-angle rf pulses. With conventional high-speed imaging approaches, however, each localization (which is typically only two-dimensional) requires the number of rf pulses needed to obtain a full image (i.e. 64 or greater). Consequently, the rf power required for "point source" tracking is much less than that required for conventional imaging and filter circuitry to minimize rf-induced heating of the catheter during "point source" tracking is not required.

System 100 further comprises EP system 160 for measuring electrical activity. In embodiments of the present invention, EP is a broad term that covers that covers a variety of procedures to treat arrhythmias of the heart, including but not limited to measuring electrical activity, delivering treatment, such as electrical mapping, pacing selectively destroying cardiac tissue, and the like. In an exemplary embodiment, EP system comprises a GE CardioLab™ 7000 system.

Processor 140 is adapted to perform several functions. In a first embodiment, processor 140 is adapted to combine the position data corresponding to the position of the catheter 120 as well as the EP measurement data. In an embodiment of a method for imaging in an image-guided interventional procedure, the method comprises acquiring volumetric image data for an anatomical region of interest; acquiring position data for a catheter inserted in the region of interest; obtaining electrophysiological (EP) measurements for the region of interest; and, combining the image data, position data and EP measurements into a resultant image for use in the interventional procedure. Image data could include MR images from gradient recalled echo (GRE), spin echo (SE), fast spin echo (FSE), steady state free precession (SSFP), echo-shifted fast GRE (ESFGRE), phase contrast (PC) magnetic resonance angiography (MRA) and myocardial delayed enhancement (MDE) images.

Referring to FIG. 4, an exemplary display using techniques of the present invention is shown. In an embodiment, the displayed image comprises a three-dimensional display 300 with the position of the catheter 260 and the EP measurements being superimposed in a color mapped display to show different colored regions 310, 320 and 330 of electrical activity and catheter position. In a further embodiment, the display is a surface-rendered 3D image and position of the catheter and EP measurements superimposed thereon. In an embodiment of a color-mapped display, the display comprises displaying data representative of the EP measurements by at least one selected algorithm. The color mapped display of electrophysiology (EP) activity may be used to guide electrical mapping and pacing. In a further embodiment, display 150 is used to guide the catheter 120 for radio-frequency (RF) ablation.

To generate a surface rendered three-dimensional (3D) image of the anatomical region, the EP measurements are converted to a form more easily visualized such as a color-mapped display using any known techniques for converting signals into a color-coded display. In an embodiment, the EP measurements may be obtained by: creating a list of surface points and normal vectors representing a surface of the region of interest in order to reconstruct a surface-rendering; and taking a series of electrical activity, e.g. voltage measurements, with the catheter and recording the coordinates of the voltage measurements. A sphere diameter may be selected by the user to display the voltage color scale. The distance between each surface point and the catheter coordinates are calculated. Each surface point may be colored by the voltage scale of the closest catheter point if the distance is less than the selected sphere radius. The colored surface is then projected onto the display and shaded using the surface normal. In an embodiment, a set of 128 colors was selected to represent various levels of electrical activity. Coordinates x, y and z and activity are written into a tracking file. The file is read by processor 140 and the activity data is converted to respective color(s). It is to appreciated that various surface rendering techniques may be used to obtain a color-mapped display.

In further embodiments, the display mode may be configured to display in cine mode or other real-time display modes employing the substantially real-time tracking according to methods of the present invention.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of performing an image-guided interventional procedure comprising:
   acquiring volumetric magnetic resonance image data for an anatomical region of interest, wherein the volumetric magnetic resonance image data comprises three dimensional (3D) magnetic resonance angiography (MRA) images and perfusion images and diffusion weighted images;
   acquiring position data for at least one catheter inserted in the region of interest, wherein the position data is obtained by a magnetic resonance imaging device via at least one tracking coil disposed within the at least one catheter;
   obtaining electrophysiological (EP) measurements with the at least one catheter for the region of interest;
   combining the image data, position data and EP measurements into a resultant image for use in the interventional procedure, wherein the resultant image comprises a surface rendered three-dimensional (3D) image of the anatomical region of interest;

superimposing a real-time, 3D position of the catheter and EP measurements on the resultant image, wherein the real-time, 3D position of the catheter is derived from magnetic resonance (MR) signals and the at least one tracking coil; and using the resultant image to guide the interventional procedure, the interventional procedure comprising radiofrequency (RF) ablation, electrical mapping, electrical pacing and combinations therefrom performed by the at least one catheter.

2. The method of claim 1 wherein the image data is acquired using a magnetic resonance imaging (MRI) scanner.

3. The method of claim 1 further comprising delivering electrophysiological treatment or therapy.

4. The method of claim 1 further comprising displaying data representative of the EP measurements by at least one selected color.

5. The method of claim 2 wherein the MRI scanner is configured to reconstruct a volumetric image from the volumetric image data.

6. The method of claim 2 wherein the catheter comprises three (3) or more tracking coils coupled to respective receiver channels of the MRI scanner and wherein the 3 or more tracking coils are used to locate coordinates of the catheter.

7. The method of claim 1 wherein a first catheter is employed for an image-guided interventional procedure and a second catheter is employed to stimulate the anatomical region of interest during the interventional procedure.

8. The method of claim 1 wherein the position data of the at least one tracking coil is obtained using point source tracking.

* * * * *